(12) United States Patent
Lightman et al.

(10) Patent No.: US 10,835,164 B2
(45) Date of Patent: Nov. 17, 2020

(54) FLUID SAMPLING APPARATUS AND METHOD

(71) Applicant: University of Bristol, Bristol (GB)

(72) Inventors: Stafford Louis Lightman, Bristol (GB); Jack Albert Leendertz, Bristol (GB); Ragini Bhake, Bristol (GB)

(73) Assignee: University of Bristol, Bristol (GB)

( * ) Notice: Subject to any disclaimer, the term of this patent is extended or adjusted under 35 U.S.C. 154(b) by 313 days.

(21) Appl. No.: 15/693,805

(22) Filed: Sep. 1, 2017

(65) Prior Publication Data

US 2017/0360344 A1     Dec. 21, 2017

Related U.S. Application Data

(62) Division of application No. 14/429,818, filed as application No. PCT/GB2013/052471 on Sep. 20, 2013, now abandoned.

(30) Foreign Application Priority Data

Sep. 21, 2012 (GB) .................................. 1216900.9

(51) Int. Cl.

| A61B 5/15 | (2006.01) |
|---|---|
| A61B 5/155 | (2006.01) |
| A61B 5/145 | (2006.01) |
| A61B 5/157 | (2006.01) |

(52) U.S. Cl.
CPC .... *A61B 5/150992* (2013.01); *A61B 5/14525* (2013.01); *A61B 5/14528* (2013.01); *A61B 5/14546* (2013.01); *A61B 5/155* (2013.01); *A61B 5/157* (2013.01); *A61B 5/150099* (2013.01); *A61B 5/150221* (2013.01); *A61B 5/150229* (2013.01); *A61B 5/150755* (2013.01); *A61B 2560/0257* (2013.01)

(58) Field of Classification Search
CPC . A61B 5/50992; A61B 5/14525; A61B 5/155; A61B 2560/0257; A61B 5/150755; A61B 5/150992; B01L 2200/0605; B01L 2200/0673; B01L 2200/16; G01N 2001/2267; G01N 1/18; G01N 2035/0237; G01N 2035/1034; G01N 2015/0007; G01N 2015/0011; G01N 2015/0023; G01N 35/08
See application file for complete search history.

(56) References Cited

U.S. PATENT DOCUMENTS

| 5,520,817 | A | 5/1996 | Anahara |
|---|---|---|---|
| 6,130,098 | A * | 10/2000 | Handique ............. B01F 5/0085 366/DIG. 2 |
| 2010/0145175 | A1 | 6/2010 | Soldo et al. |
| 2010/0240964 | A1 | 9/2010 | Sterling et al. |
| 2011/0077480 | A1 | 3/2011 | Bloom et al. |
| 2014/0128823 | A1 | 5/2014 | Odland et al. |

* cited by examiner

*Primary Examiner* — Brian R Gordon
(74) *Attorney, Agent, or Firm* — Hall Estill Attorneys at Law; Tyler J. Mantooth

(57) ABSTRACT

A sampling apparatus can have an elongate tube and a liquid partitioning unit, first port can receive an incoming flow of test liquid and a second port may be coupled to the elongate tube. The liquid partitioning unit can combine the flow of test liquid with a plurality of partitioning elements to define a plurality of discrete liquid samples for movement along and storage in the elongate tube.

5 Claims, 5 Drawing Sheets

FLUID SAMPLING APPARATUS AND METHOD

RELATED APPLICATION

The present application is a divisional of U.S. patent application Ser. No. 14/429,818 filed Mar. 20, 2015, now abandoned, which is a 35 USC 371 of PCT/GB2013/052471 filed Sep. 20, 2013 which claims priority to Great Britain Patent Application GB1216900.9 filed Sep. 21, 2012, which granted on Mar. 31, 2015, the contents of which are hereby incorporated by reference

BACKGROUND

There are many applications in which it is desirable to monitor a property of a fluid stream. One way of achieving this is to periodically sample the fluid stream to obtain a plurality of individual fluid samples. The individual samples may be collected and stored in containers, which isolate the samples from one another and can also be marked with temporal information for later analysis.

One example of the above-mentioned type of fluid sampling occurs in microdialysis. Microdialysis is a well-established, common clinical and experimental procedure and involves insertion of a narrow bore sterile probe, with a semi-permeable membrane of a certain length and character, into a body compartment of interest, such as subcutaneous tissue or within the venous compartment. An isotonic fluid is passed through the probe and biological substances of interest pass into this fluid for subsequent analysis. Effluent dialysate emerges as a continuous flow and has to be collected manually, or via large bench-top fraction collectors, into individually marked containers.

One particular field in which it is desirable to monitor a property of a fluid stream is in the measurement of hormones known to have a diurnal and/or ultradian rhythm. The normal diurnal rhythm of hypothalamic-pituitary-adrenal (HPA) activity is characterised by a nadir around midnight, rising in the early morning to a peak around 8.00 am followed by a gradual decline. Superimposed on the diurnal rhythm is a more frequent ultradian rhythm composed of secretory pulses as frequent as every one to two hours (Young E A, Abelson J, Lightman S L Front Neuroendocrinol. 2004 July; 25(2):69-76). In routine clinical practice, the diurnal rhythm is often inferred from two, or a few isolated time-point measurements in the blood or saliva (Nieman L et al J Clin Endocrinol Metab 2008 93 1526-1540), while often, pharmacological manipulation has to be employed to interrogate the HPA axis (Nieman L et al J Clin Endocrinol Metab 2008 93 1526-1540, Burk et al. Psychoneuroendo 2005 30(9) 846-865). Considering the nature of diurnal and ultradian variation, single or only a few measurements are inadequate.

SUMMARY

According to a first aspect of the invention, there is provided a fluid sampling apparatus comprising:
an elongate tube; and
a fluid partitioning unit comprising:
    a first port arranged to receive an incoming flow of test fluid; and
    a second port arranged to be coupled to the elongate tube,
wherein the fluid partitioning unit is arranged to combine the flow of test fluid with a plurality of partitioning elements to define a plurality of discrete temporally organised fluid samples for movement along and storage within the elongate tube.

Thus, the apparatus according to the first aspect provides a simple means of continuous fluid sampling, in contrast to the known container-based approach. The plurality of discrete fluid samples may be moved into the tube and, once a required quantity are within the tube, the driving force causing the fluid samples to move may be removed such that the fluid samples within the tube may remain stored within the tube. The apparatus may therefore enable uninterrupted fluid sampling over a long period of time, which is advantageous in comparison to a subject, such as a human, being connected to a bench-top collecting apparatus that limits mobility and is an abnormal constraint on normal activities. A clinical facility necessary for known bodily fluid sampling methods may introduce an element of artificial stress as it is an environment alien to the individual. The apparatus and method of the present invention allow multiple discrete samples of bodily fluid to be obtained from a subject, such as a human, undergoing a normal pattern of 24 hour activity in their own home/work environment without pain, stress, blood loss or physical inconvenience to the subject, including nocturnal collection during sleep. This may be particularly advantageous when the fluid sampling apparatus is sampling a test fluid containing cortisol or the like, which can be affected by the human's response to the sampling.

The elongate tube and/or partitioning elements may be arranged to maintain the structure of the plurality of discrete fluid samples within the tube. In some embodiments the elongate tube and/or partitioning elements are arranged to maintain the structure of the plurality of discrete fluid samples within the tube while the ends of the tube are open to atmosphere. In other embodiments the elongate tube and/or partitioning elements are arranged to maintain the structure of the plurality of discrete fluid samples within the tube when at least one end of the elongate tube is closed in a substantially fluid-tight manner; for example, by a cap. The bore of the tube may be circular, or any other suitable shape.

Thus, the elongate tube may be used to store, transport etc. collected fluid samples.

The test fluid may comprise a liquid.

The fluid partitioning unit may be arranged to introduce the partitioning elements in succession into the flow of test fluid.

Thus, the test fluid may be an uninterrupted flow, in contrast with apparatus in which a test fluid is periodically injected into a carrier fluid. Embodiments in which the fluid partitioning unit is arranged to introduce the partitioning elements in succession into the flow of test fluid may widen the possible sources of test fluid to include fluids such as bodily fluid.

The partitioning elements may comprise globules of a second fluid which is immiscible with respect to the test fluid. The second fluid may comprise a liquid, or a gas that is non-reactive and/or insoluble with respect to the test fluid.

Thus, the partitioning elements may be formed from a substance that is simple to manipulate in comparison to a solid partitioning element.

The elongate tube may be arranged to store a sufficient quantity of discrete fluid samples to enable uninterrupted sampling at a flow rate of at least 1 µL/min for at least four hours, eight hours, ten hours, twelve hours, preferably at least twenty four hours and in some cases at least seventy two hours; for example, the length of the tube may be selected to match the required volume of fluid samples and partitioning elements.

The fluid sampling apparatus may include a control pump operable to force the plurality of discrete fluid samples towards the elongate tube.

Thus, the apparatus according to embodiments of the invention can bias the discrete fluid samples into the tube, which enables use of the apparatus in situations where the pressure required to move the column of discrete fluid samples further into the tube is greater than the pressure of incoming test fluid.

The fluid sampling apparatus may include a pressure sensor arranged to measure fluid pressure within the first port and a control circuit arranged to monitor the pressure difference between the fluid within the first port and a reference pressure and generate a control signal operable to modify the operation of the control pump accordingly. The fluid sampling apparatus may include a pressure sensor arranged to measure local atmospheric pressure outside of the fluid sampling apparatus and wherein the reference pressure comprises the measured local atmospheric pressure.

Thus, the apparatus according to embodiments of the invention can control operation of the pump to ensure that the fluid pressure at the first port is substantially constant, which can be desirable in applications such as when the first port is coupled to a medical or veterinary device, or other device suitable for pumping test fluid into the fluid sampling apparatus at a controlled flow rate.

The elongate tube may be arranged to retain the plurality of discrete fluid samples when uncoupled from the fluid partitioning unit.

The elongate tube may be arranged in a coiled configuration. This may be achieved by a bracket or strap which maintains the coiled arrangement.

Thus, the elongate tube may be arranged in a compact configuration that lends itself to portability.

The fluid sampling apparatus may be arranged such that each discreet fluid sample is longer than it is wide.

The tube may be formed of a material having one or more of the following properties:
  a fluidphobic material, such as a hydrophobic material;
  an inert material;
  a transparent or translucent material.

The first port of the partitioning unit may be arranged to be coupled to, or in combination with, a medical device, such as a microdialysis device.

Thus, the apparatus may provide a solution to the problem of how to obtain a full 24 hour profile of hormones that are known to cycle both on a daily (diurnal) and near hourly (ultradian) fashion. This can be very important as abnormalities are often the most clinically relevant during the time of the hormonal nadir when hormone levels are at their lowest. This time is—for cortisol—between midnight and 3.00 am—times at which routine sampling techniques are difficult. In some embodiments the apparatus may be arranged to sample a test fluid containing prescription drugs or experimental drugs, which may be useful in clinical trials or monitoring drug therapy. In some embodiments the apparatus may be arranged to sample a test fluid containing drug metabolites and/or other suitable biomarkers for clinical trials.

The components of the apparatus may be selected to have a total mass of less or equal to 20 kg, and preferably less than or equal to 1 kg. The fluid partitioning unit may be encapsulated within a housing arranged to be comfortable for a user to wear, and non-intrusive.

Thus, the apparatus may be portable and wearable for a long period of time, enabling fluid sampling from a human or other animal body over a prolonged period.

According to a second aspect of the invention, there is provided a method of processing and storing a test fluid, the method comprising the steps of:
  combining a flow of test fluid with partitioning elements to partition the flow of test fluid into a plurality of discrete fluid samples; and
  delivering the plurality of discrete fluid samples to an elongate tube for storage.

The steps of combining and delivering may continue for at least twenty four hours.

The partitioning elements may be combined with the test fluid at a frequency of at least 1 per hour so that the discrete fluid samples are partitioned into time dependent increments.

The test fluid may comprise one or more substances of interest such as proteins, steroids, drugs or other chemical compounds. In one embodiment of the invention a substance of interest may be a hormone, preferably a hormone which shows circadian variability such as a diurnal and/or ultradian rhythm. Hormones of interest may include gonadotrophin-releasing hormone (GnRH), luteinizing hormone (LH), follicle stimulating hormone (FSH), prolactin, testosterone, growth hormone, melatonin, thyroid stimulating hormone (TSH), insulin, parathyroid hormone (PTH), adrenocortocotrophic hormone (ACTH) and cortisol. Preferably the hormone is cortisol, growth hormone or insulin. In a further embodiment of the invention the substances of interest may include catecholamines such as epinephrine (adrenaline), norepinephrine (noradrenaline) and dopamine. Other substances of interest may include lactic acid and glucose. In a yet further embodiment of the invention the substance of interest may include a drug or metabolite.

According to a further aspect of the present invention, there is provided an elongate tube arranged or specially adapted for use with apparatus according to the first aspect and/or use in a method according to the second aspect.

The method may further comprise separating the plurality of discrete fluid samples from one another and analysing the samples for the one or more substances of interest.

BRIEF DESCRIPTION OF THE DRAWINGS

Embodiments of the invention will now be described with reference to the accompanying drawings, in which.

DETAILED DESCRIPTION

Figure 1:
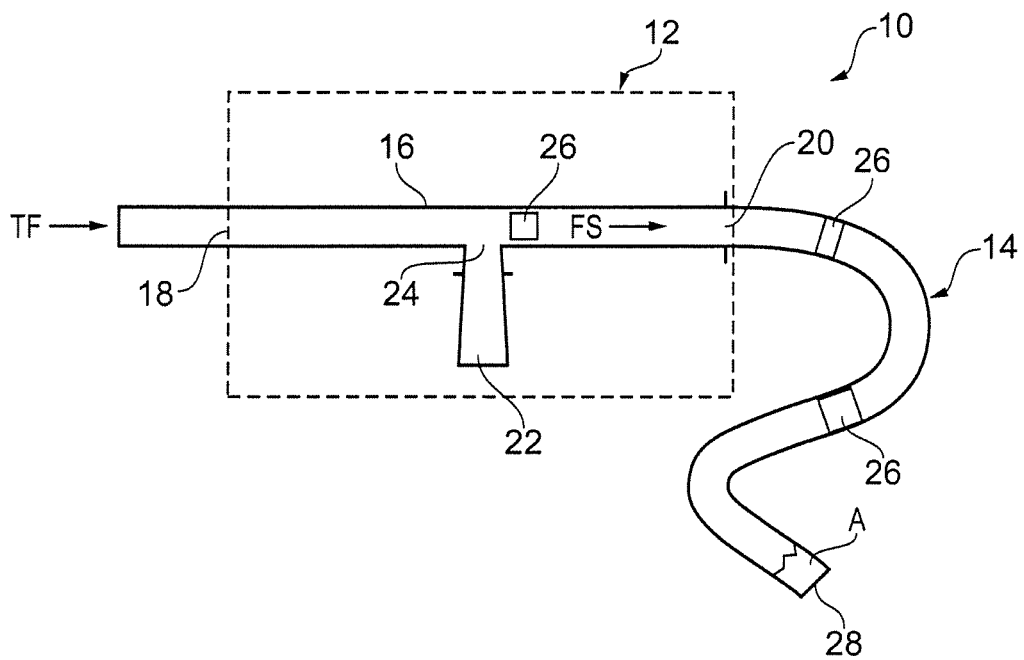
FIG. 1 is a diagram of fluid sampling apparatus according to an embodiment of the invention.

FIG. 1 shows fluid sampling apparatus 10 according to an embodiment of the invention. As an overview, the fluid sampling apparatus 10 has a fluid partitioning unit 12 arranged to receive a flow of test fluid TF and partition it into a plurality of individual fluid samples FS, and an elongate tube 14 arranged to store the plurality of individual fluid samples FS.

The fluid partitioning unit 12 defines a fluid passage 16 having a first port 18 and a second port 20.

The first port 18 is arranged to be coupled to a source of test fluid (not shown) to define a substantially fluid-tight passageway between the fluid partitioning unit 12 and the source of test fluid to receive the flow of test fluid TF. The test fluid TF is a fluid that contains a substance of interest and as such is to be sampled. The test fluid TF may be a liquid or a gas. Preferably the test fluid TF is a bodily fluid, such as blood or cerebrospinal fluid. Where the test fluid TF is blood, anticoagulation fluid should be added. In a preferred embodiment of the invention the test fluid TF is microdialysate.

The second port 20 is arranged to be coupled to the elongate tube 14 to define a substantially fluid-tight passageway between the fluid partitioning unit 12 and the elongate tube 14.

The first port 18 and second port 20 may define any suitable connection type, such as a sleeve or collar sized to form an interference fit with a resiliently deformable tube. In some embodiments the first port 18 and/or second port 20 may define a Luer or Luer Lock fitting.

A partitioning element insertion unit 22 is coupled to the fluid passage 16 via a third port 24 located between the first port 18 and second port 20. The partitioning element insertion unit 22 is arranged to insert partitioning elements 26 into the flow of test fluid TF to create a plurality of discreet fluid samples FS that are delivered to the elongate tube 14 via the second port 20. The fluid partitioning unit is arranged to introduce the partitioning elements 22 in succession into the flow of test fluid TF. In some embodiments, partitioning elements 22 may be introduced with 1.25, 2.5, 5, 10, 20, 30 or 60 minutely frequency, although any suitable and/or desirable frequency may be used. Thus, in some embodiments the discrete fluid samples may be taken at intervals of from about 1 minute to 4 hours, in some embodiments from about 1 minute to about 1 hour, preferably from about 1 minute to about 20 minutes, most preferably about 10 minutes. In some embodiments it is desirable for the fluid samples to be taken at intervals of from about 10 minutes to 1 hour.

The partitioning elements 26 may take any suitable form that effectively partitions the test fluid TF and can be moved along the elongate tube 14. In some embodiments the partitioning elements 26 may be globules or bubbles of a fluid that is generally immiscible with respect to the test fluid TF. For example, the second fluid may comprise a gas that is non-reactive and/or insoluble with respect to the test fluid TF. Preferably the second fluid is an inert gas, such as nitrogen or argon. In a preferred embodiment of the invention the second fluid is air. In other embodiments, the partitioning elements 26 may be solid objects sized to match the inner diameter of the elongate tube 14, although a fluid is preferred for the partitioning elements 26 because a fluid partitioning element may conform better to the inner diameter of the elongate tube 14, may be lighter than a solid partitioning element and may be simpler to manipulate into the stream of test fluid TF.

The elongate tube 14 is arranged to store the plurality of discreet fluid samples FS. In the illustrated embodiment, the distal opening 28 of elongate tube 14 with respect to the opening coupled to the second port 20 is open to the atmosphere so as to allow air A within the elongate tube 14 to egress as the plurality of discreet fluid samples FS are moved into the tube 14 for storage.

The fluid sampling apparatus 10 is arranged to maintain the structure of plurality of individual fluid samples FS such that the fluid samples do not mix with one another.

In some embodiments, the fluid sampling apparatus 10 may be arranged to dispense partitioning elements 26 into test fluid TF of a particular flow rate such that each discreet fluid sample is longer than it is wide. This may promote stability of each individual fluid sample, which is advantageous in embodiments where the partitioning elements 26 are in the form of a fluid. The length of a fluid sample may refer to its axial dimension, whereas its width may refer to the internal diameter of the tube 14.

The elongate tube 14 according to embodiments of the invention may be formed of a fluidphobic material having a low degree of wetting with respect to the test fluid. As will be appreciated by the skilled person, 'wetting' is a measure of a liquid's ability to maintain contact with a solid surface due to intermolecular interactions when the liquid and solid are brought together. The degree of wetting is determined by a force balance between adhesive and cohesive forces. Thus, where the degree of wetting is low, the fluid within the elongate tube 14 is more inclined to remain in a globule than it is to flatten and mix with an adjacent globule. A high surface tension increases the force needed to move fluid partitioning elements 26 along the elongate tube 14. Where the test fluid comprises water, the elongate tube 14 may therefore be formed of a hydrophobic material. Suitable materials include perfluoroalkoxy (PFA) and fluorinated ethylene propylene (FEP), in a preferred embodiment of the invention the elongate tube is formed of polytetrafluoroethylene (PTFE). In embodiments where the partitioning elements 26 are formed of a liquid that is generally immiscible with respect to the test fluid TF, it may be advantageous for the elongate tube 14 to be formed of an oleophobic material that preferably also exhibits a low degree of wetting with respect to the test fluid. Preferably the material is inert and has a low binding affinity for proteins.

The resistance to droplet motion, due to surface tension, will decrease with a decrease in tube diameter. If the tube diameter is reduced by a factor of 2, say, then the force will reduce by a factor of 2. However, the cross-sectional area of the tube will reduce by a factor of 4, so that pressure will need to increase by a factor of 2 to overcome the resistance. In some embodiments, particularly those where it is important for the apparatus to be portable or usable for long periods of time without interruption, this may have implications for the internal cross-sectional area of the elongate tube 14; for example, the tube 14 may be sized to avoid a high pressure build up within the elongate tube 14.

The flow rate of test fluid TF may be from about 0.01 to about 50 µL/min, preferably about 0.1 to about 10 µL/min, more preferably about 0.1 to about 5 µL/min. In a preferred embodiment of the invention the flow rate is about 2 µL/min. The device of the present invention may be used for uninterrupted sampling over a period of about 1 hour to about 72 hours, preferably about 12 hours to about 48 hours, most preferably about 24 hours. In some embodiments the elongate tube 14 is arranged to store a sufficient quantity of discrete fluid samples to enable uninterrupted sampling at a flow rate of at least 1 µL/min for at least twenty four hours.

In some embodiments the elongate tube 14 is has an internal diameter sized to inhibit mixing between the plurality of discreet fluid samples FS through fluid partitioning elements 26; for example, the tube 14 may have an internal diameter of 1 mm and the apparatus 10 controlled such that the fluid samples each have a size of 20 uL, which gives a sample length of approx. 25 mm. For 144 samples (24 hrs at 10 min) this may give rise to 0.3 to 0.5 atmosphere pressure to move the column of fluid samples along the tube 14. If the tube 14 diameter is halved the pressure may double, meaning that the pump or pumps driving the test fluid TF and/or plurality of discreet fluid samples FS would be under greater stress and connectors may need to be enhanced to inhibit leakage. If the tube diameter 14 is doubled to 2 mm, the plurality of discreet fluid samples FS may each be about 6 mm long and 2 mm in diameter. The skilled person will see from this that there is a complex relationship between tube diameter, sample interval, flow rate and duration and, due to this, applications may have to be assessed individually. Building on the above, if the tube diameter is increased to 3 mm diameter, the plurality of discreet fluid samples FS may each have a width that is greater than their length, which may provide an unstable configuration with fluid partitioning elements 26, so in such cases solid partitioning elements 26 should be used.

In embodiments where solid partitioning elements are provided, larger diameter elongate tubes may be used. In some embodiments it may be desirable to provide a pressure release valve at the distal opening 28 of the elongate tube 14 to enable the fluid pressure within the distal end region of the tube to be greater than atmospheric pressure while still enabling a plurality of discreet fluid samples FS to be moved along the elongate tube 14.

The elongate tube 14 may advantageously be arranged in a coiled configuration. This may be achieved by a bracket or strap which maintains the coiled arrangement, or the tube may be wound around a spool. Such configurations advantageously reduce the envelope of the elongate tube.

In use, the fluid sampling apparatus 10 according to the illustrated embodiment may be coupled to a source of test fluid TF. The fluid partitioning unit 12 combines the flow of test fluid TF with the partitioning elements 26 to partition the flow of test fluid TF into a plurality of discrete fluid samples FS which are delivered to the elongate tube 14 for storage. Once a predetermined number of discrete fluid samples FS have been moved into the elongate tube 14, the elongate tube can be uncoupled from the fluid partitioning unit 12 for analysis.

In some embodiments the elongate tube 14 is arranged to retain the plurality of discrete fluid samples FS when uncoupled from the fluid partitioning unit; for example, the internal diameter may be sized such that the pressure required to move the plurality of discrete fluid samples FS along the tube is greater than the pressure exerted due to gravity. In other embodiments, an end cap or other covering means (not shown) may be provided to close one or both ends of the elongate tube 14 to inhibit egress of the plurality of discrete fluid samples FS following uncoupling of the elongate tube 14 from the fluid partitioning unit 12.

In some embodiments the distal opening 28 of the elongate tube 14 may be provided with a one way valve to permit air to egress from the elongate tube 14, but inhibit fluid entering.

The components of the apparatus 10 may be selected to have a total mass of less or equal to 20 kg, and preferably less than or equal to 1 kg. The fluid partitioning unit 12 may be encapsulated within a housing arranged to be comfortable for a user to wear, an non-intrusive. Thus, the apparatus 10 may be portable and wearable for a long period of time, enabling fluid sampling from a human body over a prolonged period.

Figure 2:
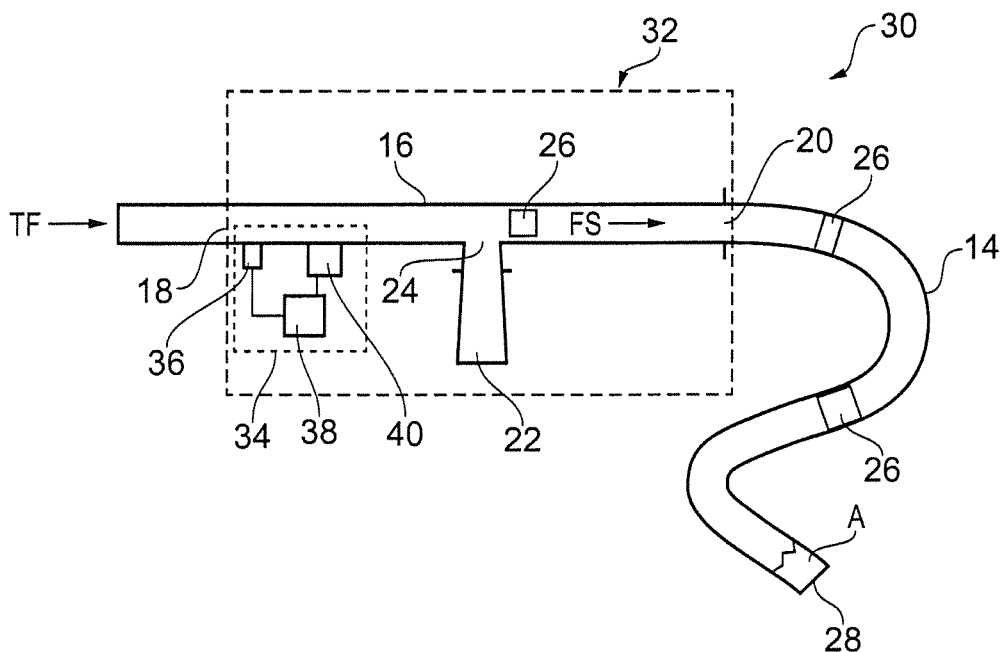
FIG. 2 is a diagram of fluid sampling apparatus according to a further embodiment of the invention.

FIG. 2 shows fluid sampling apparatus 30 according to a further embodiment of the invention. As an overview, the fluid sampling apparatus 30 of the illustrated embodiment is similar to that shown in FIG. 1 and like parts have been given the same reference numerals. However, the fluid sampling apparatus 30 of the illustrated embodiment additionally includes a pressure modifying assembly 34 arranged monitor the pressure difference between the fluid within the first port 18 and a reference pressure and generate a control signal operable to modify the operation of a control pump 40 ensure that the fluid pressure at the first port is substantially constant, which can be desirable in applications where it is undesirable to let the pressure at the first port increase, which can occur as the plurality of discreet fluid samples FS are moved into the elongate tube 14.

The pressure modifying assembly 34 includes a pressure sensor 36 arranged to measure fluid pressure within the first port 18 and a control circuit 38 arranged to monitor the pressure difference between the fluid within the first port 18 and a reference pressure, and generate a control signal operable to modify the operation of the control pump 40 accordingly. The reference pressure may be local atmospheric pressure, measured by an appropriate pressure sensor. The control circuit 38 may also be arranged to control the introduction of the partitioning elements 26 into the flow of test fluid TF.

Any suitable conventional pressure sensor 36 may be used, such as a Honeywell 26PCAFA6D.

Any suitable conventional control pump 40 may used; for example, a peristaltic pump such as a Dolomite Peristaltic Pump Part no. 3200243.

In some embodiments, it is desirable that the power consumption of the fluid sampling apparatus is low enough to utilise battery power for prolonged periods and in such cases low voltage electronic circuits, such as a maximum of 3 volts, may be provided. A low voltage circuit and/or a fuse may also increase user safety.

In use, the fluid sampling apparatus 30 according to the illustrated embodiment works in a similar manner to the apparatus 10 of FIG. 1. However, the apparatus of the illustrated embodiment additionally measures the fluid pressure within the apparatus 30 and compares the measured pressure to a reference pressure. If the two pressure values differ by more than a predetermined amount, or in some cases if a particular one exceeds the other, the pump 40 is operated to modify the pressure at the location of measurement such that the measured pressure becomes closer to the reference pressure. As such, the fluid sampling apparatus 30 according to the illustrated embodiment may be used in situations where the incoming test fluid line TF is sensitive to fluid pressure variations; for example, in microdialysis, or other applications such as blood or cerebrospinal fluid sampling.

Example 1

Figure 3:
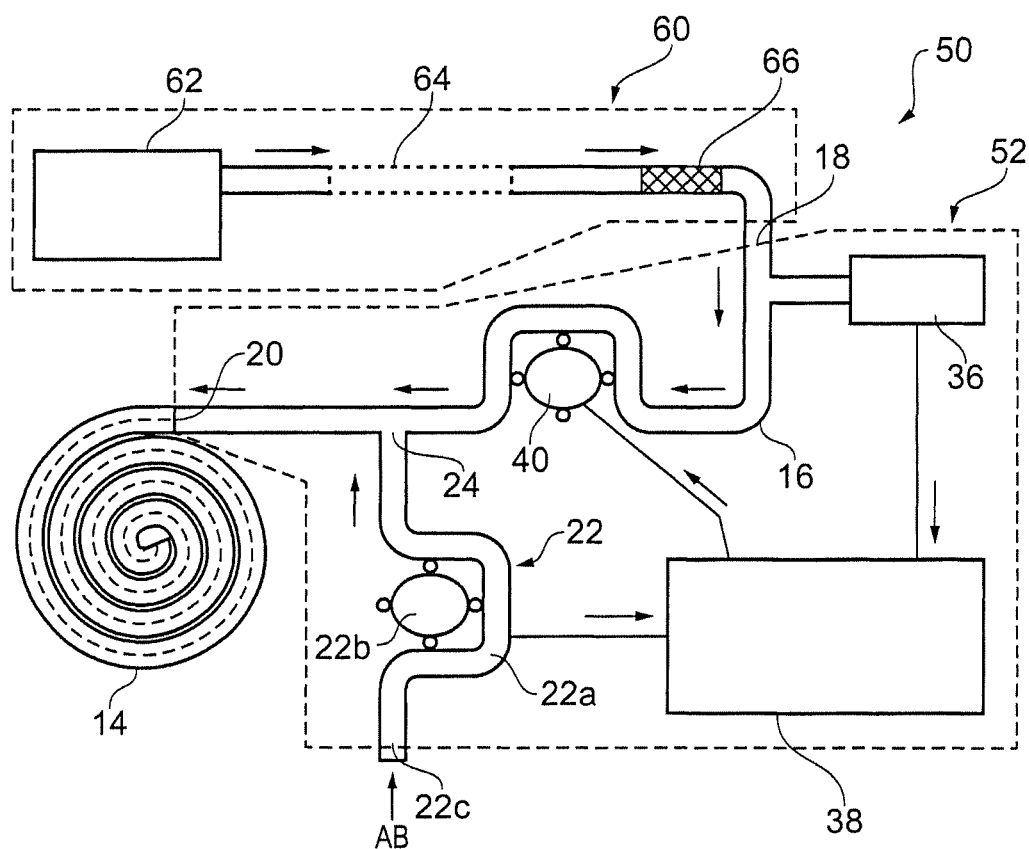
FIG. 3 is a diagram of fluid sampling apparatus according to a yet further embodiment of the invention, wherein the apparatus is arranged to be coupled to microdialysis device.

FIG. 3 shows fluid sampling apparatus 50 according to a further embodiment of the invention. As an overview, the fluid sampling apparatus 50 of the illustrated embodiment is similar to that shown in FIG. 2 in that the sampling apparatus 50 has a fluid partitioning unit 52 arranged to receive a flow of test fluid TF and partition it into a plurality of individual fluid samples FS, it has pump means 40 to control the fluid pressure, and an elongate tube 14 arranged to store the plurality of individual fluid samples FS; like parts have been given the same reference numerals. However, the fluid sampling apparatus 50 of the illustrated embodiment is arranged to be coupled to microdialysis device 60. As will be appreciated, this involves insertion of a narrow bore sterile probe 64, with a semi-permeable membrane of a certain length and character, into the body compartment of interest e.g. subcutaneous tissue or within the venous compartment, although the latter may require a different catheter in which the inlet and outlet are at one end of the probe and the semi-permeable membrane at the other end. An isotonic fluid is passed through the probe 64 and biological substances of interest pass into this fluid for subsequent analysis. The effluent dialysate emerges as a continuous flow. The microdialysis device 60 is coupled to the first port 18 via a connector 66, which is shown as being part of the microdialysis device 60 but in practice may be an external connector used to connect the microdialysis device 60 to the fluid partitioning unit 52.

As well as collecting samples at frequent intervals for a period of at least 24 hours, it is desirable that the power consumption of the fluid sampling apparatus 50 is low enough to allow us to utilise battery power only, for prolonged periods. We also provide safety features including low voltage electronic circuits (maximum of 3 volts) and a fuse to eliminate unexpected problems. We also had to demonstrate that the device was acceptable and could provide automatic collection of sampling throughout the day and night without disturbing the subject—and in particular their sleep.

Materials And Methods

Subcutaneous free cortisol was accessed using microdialysis (Cohen Crit Care 2009). A microdialysis pump 62 (CMA 107 microdialysis pump, Sweden) was used to infuse an isotonic solution through a microdialysis probe 64 inserted subcutaneously into the anterior abdominal wall. Isotonic fluid was infused through the probe at the rate of 2 microlitres/minute.

The microdialysate was then collected in our automated fluid sampling apparatus 50, the collected samples being stored in a length of polytetrafluoroethylene (PTFE) tubing 14, wrapped concentrically around a spool.

Sample Collection

The division of samples generated at different times was achieved by the injection of an air bubble at predetermined intervals. The bubbles separate individual samples which then move along the tubing 14 as new samples are introduced. This was achieved by a peristaltic pump 22b which injected bubbles from a tube 22a, open to atmosphere via an opening 22c, through a T junction 24. The pump 22b was advantageously small in size, light weight and used low current consumption. A Dolomite Peristaltic Pump Part no. 3200243 was chosen.

Maintenance of Pressure Across Microdialyis Membrane

As the number of samples in the PTFE tubing 14 increases, there is an increase in the pressure needed to move the samples along the PTFE tubing 14. This pressure increased to 0.5 atmospheres when there were 72 samples in the tube 14. In order to maintain normal pressure in the microdialysis probe 64, pressure was detected by a sensor 36 between the microdialysis probe 64 and the second port 20. The sensor 36 controlled a second identical peristaltic pump 40 that provides the pressure to move the samples along the collecting line 14.

Figure 4:
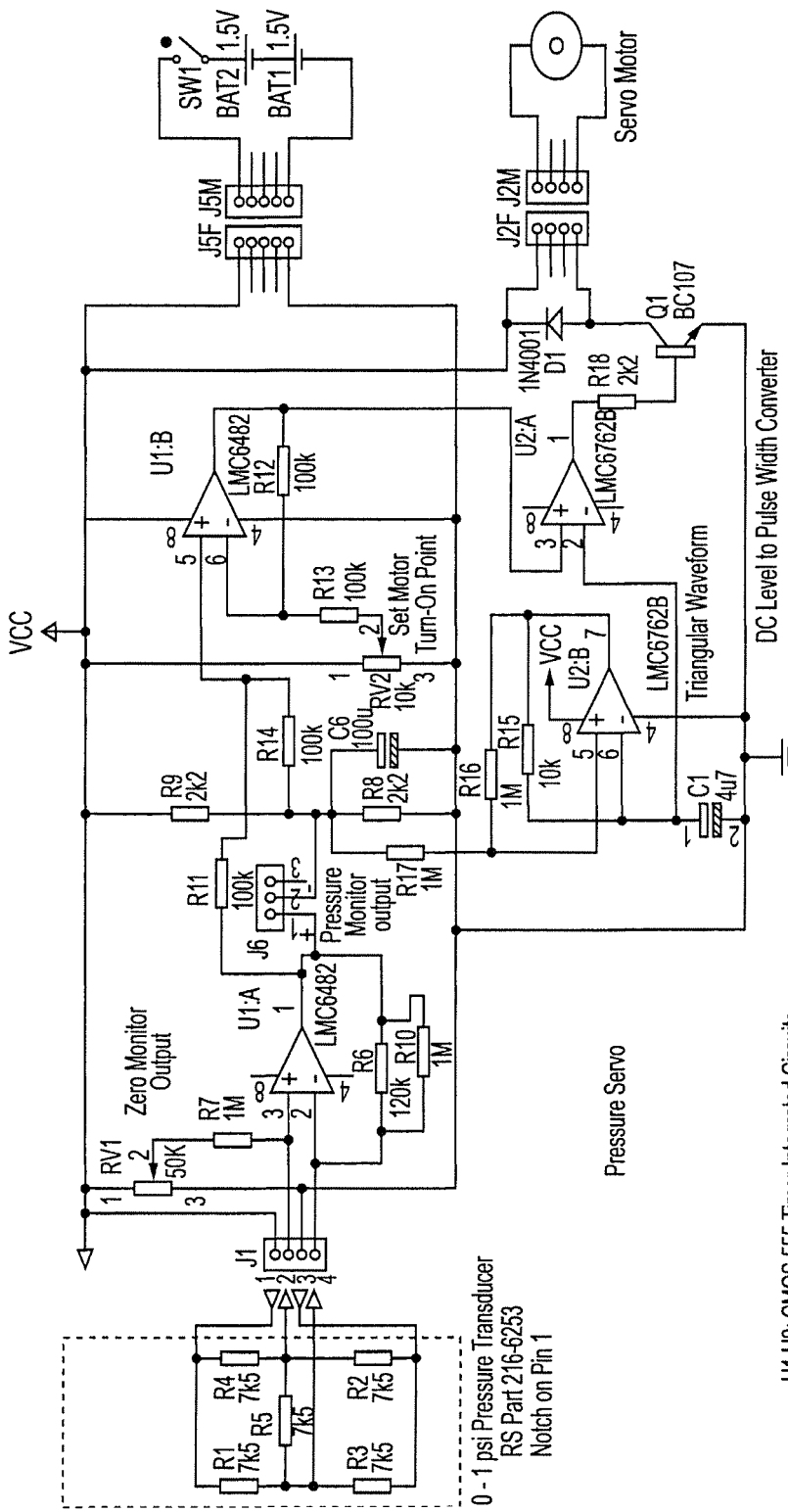
FIG. 4 shows circuit diagrams for a pressure servo and a bubble timer of specific embodiments of the invention.
Figure 4:
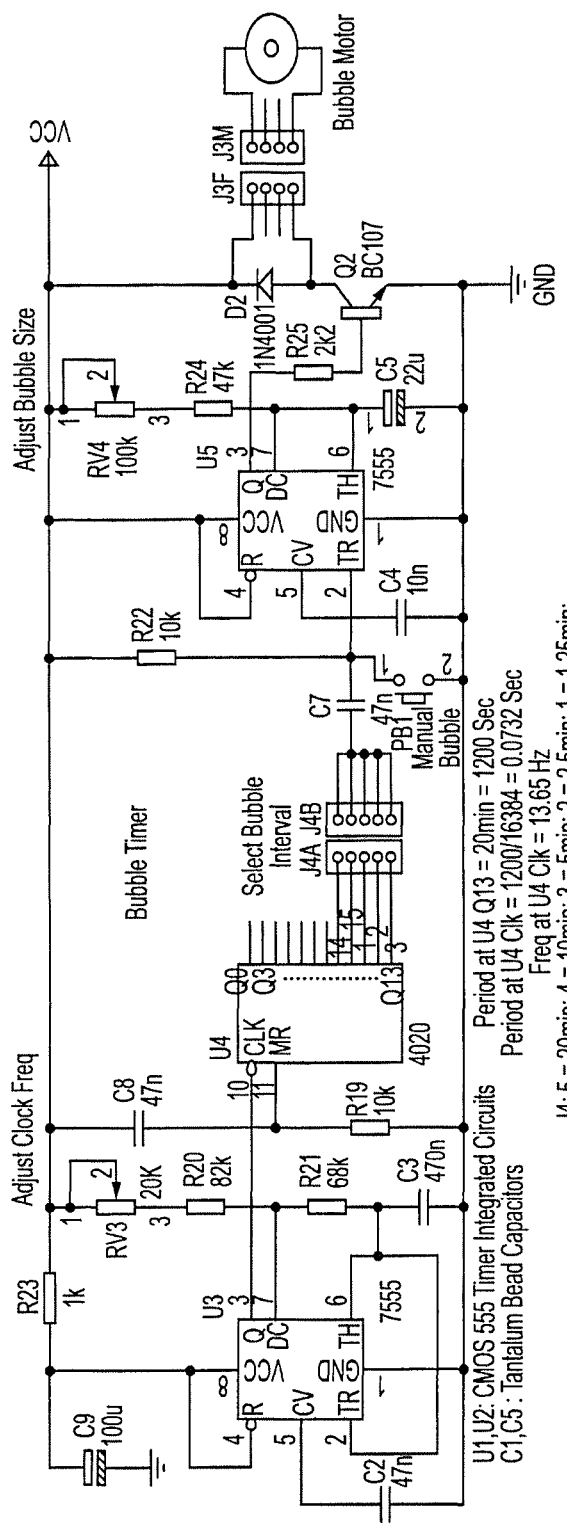

As illustrated in FIG. 4, the sensor 36 had semi-conductor piezo resistive elements in a Wheatstone bridge arrangement. The output from the bridge was fed into a high gain differential stage using U1A. RV1 was used to offset any bridge output present when the pressure is zero. The servo pump motor was driven from the pressure signal using pulse width modulation. This was necessary to maintain a high torque at low running speeds. The op-amp U2B is an oscillator which generated an approximately triangular waveform across C1. This signal was fed into the −ve input of U2A, which was used as a comparator. The +ve input was fed with the pressure signal after adding a preset DC level using op-amp U1B as a unity gain differential amplifier. The output from the comparator was fed into transistor Q1 which switched the current to the servo motor between full current and zero. As the pressure increased the full current dwell time increased driving the motor harder and thus reducing the pressure. RV2 set the probe line pressure by determining the point where the motor starts to get driven. This servo system kept the pressure constant to within about 10 cm of water pressure.

Bubble Timing

The frequency of sampling was determined by the periodiaty of the bubbles inserted in the micrdodialysate column by the U3 complementary metal-oxide semiconductor (CMOS) 555 timer. This run as an astable multivibrator to give a clock frequency of 13.65 Hz, pre-set using RV3. This clock signal was fed to U4 which is a type 4020 multi stage binary divider. The output from stage 12 had a period of 10 minutes and triggered U5. This was another CMOS 555 timer this time running in monostable mode generating a pulse of around two seconds duration, pre-set by RV4. This pulse turned on transistor Q2 which powered motor for the air bubble insertion pump.

The system was run for over 24 hours on two AA size cells of the lithium iron disulphide type.

Complete System

The dimensions of the final collection system were 152 mm×84 mm×52 mm (length×breadth×height respectively), and the weight was 400 grams. The inner components of the compact device, which is made of plastic, were accessible through its removable lid. Put another way, the components of the fluid sampling apparatus are encapsulated in a casing having a removable lid. Access to the device enables replacement of batteries and PTFE tubing.

The distal end of a linear microdialysis probe was connected to the collection system using a 15-20 cm section of fluorinated ethylene propylene (FEP) tubing and a commercially available connector 66. For the system, the most convenient site of insertion for the microdialysis probe was the lower abdominal wall.

When sampling was complete, individual samples were decanted manually into marked tubes and stored for laboratory analysis.

Participants

Ethical approval for this study was obtained from the Bath Research Ethics Committee. Six male healthy volunteers (age 18-24) gave their informed consent. The subcutaneous microdialysis probe was inserted into the anterior abdominal wall and connected up to our collection device. Interstitial fluid samples were collected at 10 minute intervals for 24 hours. The study was carried out at the local clinical research facility where the participants spent the duration of sampling. CMA 66 catheter (CMA, Sweden) was inserted subcutaneously under local anaesthesia, and connected to the collection system as described above. Once the entire system was set up, the collection device and microdialysis pump were placed in a commercially available waist-bag. Interstitial fluid samples were collected at 10-minute intervals for 24-hours.

Analytical Technique

Figure 5:
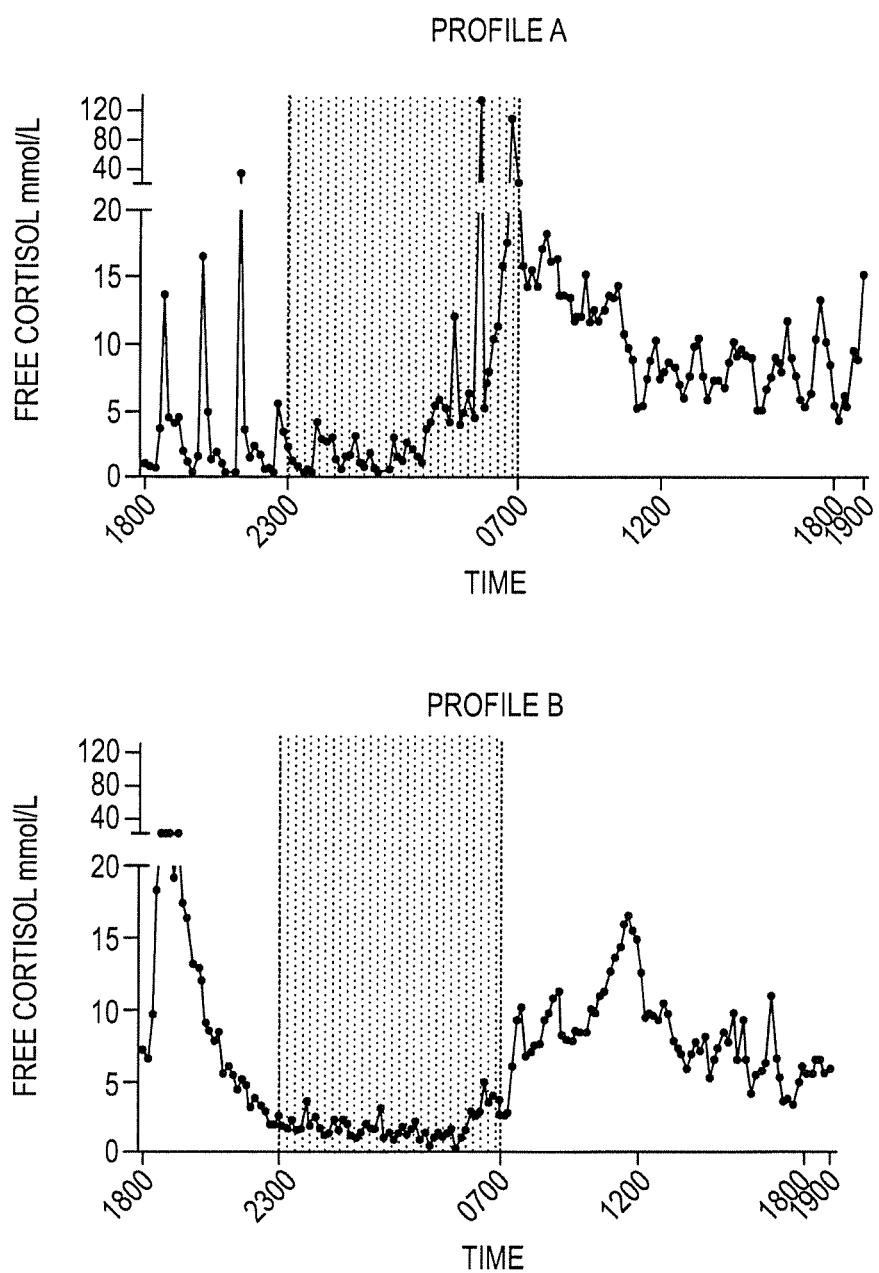
FIG. 5 shows two individual 24 hour profiles of human subcutaneous tissue free cortisol measured from samples collected using the apparatus of the present invention.

Microdialysis fluid from each timed sample was pipetted into an individual well of a 96 well plate and free cortisol measured using enzyme-linked immunosorbent assay (Saliva cortisol ELISA, IBL, Germany). The sensitivity of our assay was 0.005 µg/dL with inter- and intra-assay coefficients of variation of 9.3% and 4.2% respectively. Two typical individual 24 hour profiles of subcutaneous tissue free cortisol are seen in FIG. 5.

It was thus possible to obtain multiple discrete samples of bodily fluid from a human undergoing a normal pattern of 24 hour activity in their own home/work environment without pain, stress, blood loss or physical inconvenience to the subject. The normal pattern of 24 hour activity included nocturnal collection during sleep.

The fluid sampling apparatus 50 may have one or more of the following advantages:

1. Miniaturized portable sample collection device—the dimensions of the collection system are 152 mm×84 mm×52 mm (length×breadth×height respectively), and the weight is 400 grams. It fits comfortably, along with the microdialysis pump, within a commercial waistbag routinely available for travel purposes.

2. Undisturbed nocturnal sample collection during sleep—the device makes sample collection possible without an individual's knowledge, safely in their own environment, without causing any pain or discomfort. In some cases the individual may be completely unaware of the sampling process taking place in the background. Therefore, samples can be collected continuously throughout the night when an individual is asleep. This is a particularly advantageous feature of the device. The apparatus enables continuous, un-interfered sampling of microdialysate samples throughout sleep in an individual's home, without the need to attend a clinical facility.

3. Automated sample collection—despite technological advances of great significance in the twenty first century with numerous instances of automation in various walks of life, application of the knowledge in the field of continuous prolonged biosampling has been lacking.

4. Discrete timed sample collection and storage—the apparatus 50 has the ability to provide the approximate time of each sample fraction contained within the collection spool defining the elongate tube, due to the temporal organisation of the samples.

Although the invention has been described above with reference to one or more preferred embodiments, it will be appreciated that various changes or modifications may be made without departing from the scope of the invention as defined in the appended claims. The word "comprising" can mean "including" or "consisting of" and therefore does not exclude the presence of elements or steps other than those listed in any claim or the specification as a whole. The mere fact that certain measures are recited in mutually different dependent claims does not indicate that a combination of these measures cannot be used to advantage.

The invention claimed is:

1. A method comprising:
providing a partitioning unit defining a fluid passage having a first port and a second port;
connecting the fluid passage to a fluid source via the first port, to a storage tube via the second port, and to a first pump via a third port, the partitioning unit comprising a pressure assembly comprising a control circuit;
flowing a test fluid from the fluid source to the fluid passage with a second pump connected between the first and third ports;
inserting a partitioning material into the test fluid with the first pump;
separating the test fluid into at least a first discrete fluid sample and a second discrete fluid sample separated by partitioning material;
flowing the test fluid into the storage tube, the partitioning material filling a diameter of the storage tube to separate the first discrete fluid sample from the second discrete fluid sample in the storage tube; and
uncoupling the storage tube from the partitioning unit, the first and second discrete fluid samples remaining separated by the partitioning material.

2. The method of claim 1, wherein the pressure assembly further comprises a pressure sensor and is arranged to alter the second pump in response to a sensed change in test fluid pressure to provide a pressure differential between the first port and second port.

3. The method of claim 1, wherein the test fluid is a liquid and the partitioning material comprises a bubble of gas which is immiscible with respect to the test fluid.

4. The method of claim 3, wherein the partitioning material comprises a gas that is non-reactive and insoluble with respect to the test fluid.

5. The method of claim 1, wherein the pressure assembly comprises a further pressure sensor arranged to measure local atmospheric pressure outside of the partitioning unit and the control circuit is arranged to activate the second pump to decrease a measured difference between a reference pressure and the local atmospheric pressure.

* * * * *